(12) United States Patent
Moran et al.

(10) Patent No.: US 6,641,595 B1
(45) Date of Patent: Nov. 4, 2003

(54) LAPAROSCOPIC FORCEPS HANDLE

(75) Inventors: Peter Moran, Leeds (GB); Stuart Moran, Leeds (GB); Mike White, Leeds (GB)

(73) Assignee: Surgical Innovations Ltd., Leeds (GB)

( * ) Notice: Subject to any disclaimer, the term of this patent is extended or adjusted under 35 U.S.C. 154(b) by 89 days.

(21) Appl. No.: 09/586,677

(22) Filed: Jun. 1, 2000

(30) Foreign Application Priority Data

Aug. 20, 1999 (GB) .............................................. 9919722

(51) Int. Cl.[7] .............................................. A61B 17/28
(52) U.S. Cl. ...................................................... 606/205
(58) Field of Search ................................ 606/125, 128, 606/205–208; 81/338

(56) References Cited

U.S. PATENT DOCUMENTS

| | | |
|---|---|---|
| 5,176,702 A | 1/1993 | Bales et al. |
| 5,251,638 A | 10/1993 | Cottone, Jr. et al. |
| 5,938,667 A | 8/1999 | Peyser et al. |

FOREIGN PATENT DOCUMENTS

| | | |
|---|---|---|
| FR | 2 688 681 | 9/1993 |

*Primary Examiner*—Michael J. Milano
*Assistant Examiner*—P Roberts
(74) *Attorney, Agent, or Firm*—Beyer Weaver & Thomas LLP

(57) ABSTRACT

A laparoscopic forceps comprising a handle; a tubular housing extending axially from the handle and carrying an actuator rod; a jaws mechanism disposed at the end of the tubular housing remote from the handle engaged to the actuation rod and arranged so that the jaws may be opened or closed by actuation of the handle; wherein the handle comprises left and right bow members pivotally connected to a mounting core in a scissors-like arrangement, and adapted to engage a user's finger and thumb in use;

the forceps including a switchable ratchet mechanism moveable between locked and unlocked positions, adapted when locked to allow closure and prevent opening of the jaws, and when unlocked to allow free opening and closing of the jaws.

20 Claims, 5 Drawing Sheets

LAPAROSCOPIC FORCEPS HANDLE

TECHNICAL FIELD

This invention relates to laparoscopic forceps, particularly to the handle of such forceps.

BACKGROUND

Laparoscopic forceps conventionally comprise a handle, a tubular housing carrying an actuator mechanism and a forceps jaws mechanism located at the remote end of the tubular housing. Manual actuation of the handle opens or closes the jaws. The shaft and jaws mechanism may be rotated relative to the handle and a ratchet mechanism may be provided to allow clamping of the jaws. A monopolar diathermy connection may be provided to facilitate cauterisation of tissue clamped by the jaws. In conventional laparoscopic forceps the handle comprises a pistol grip arrangement wherein the diathermy connection extends upwardly so that the power cable extends from the handle over a surgeon's hand adjacent the knuckles or thumb. The pistol grip arrangement makes it necessary for a surgeon to raise or lower the elbow in order to rotate the forceps in use. This is inconvenient and can be tiring, particularly as the diathermy cable may pass over the surgeon's elbow.

SUMMARY

According to the present invention a laparoscopic forceps comprises a handle; a tubular housing extending axially from the handle and carrying an actuator rod; a jaws mechanism disposed at the end of the tubular housing remote from the handle engaged to the actuation rod and arranged so that the jaws may be opened or closed by actuation of the handle; wherein the handle comprises left and right bow members pivotally connected to a mounting core in a scissors-like arrangement, and adapted to engage a user's finger and thumb in use; the forceps including a switchable ratchet mechanism moveable between locked and unlocked positions, adapted when locked to allow closure and prevent opening of the jaws, and when unlocked to allow free opening and closing of the jaws.

Laparoscopic forceps in accordance with the present invention confer the advantage that the operation and positioning of the jaws may be controlled by the thumb and one finger of the surgeon, leaving fingers free for operation of the switchable ratchet mechanism or other tasks.

The construction and function of the forceps of this invention may be considered conveniently with the scissor-like bows generally horizontal so that a surgeon's hand is in the prone position with palm downwards during use.

The switchable ratchet mechanism preferably incorporates a finger operable switch member. The switch member is preferably located on the upper side of the mounting core of the handle. In preferred embodiments the switch extends longitudinally of the handle, and is engaged by a pivot at the rear end thereof between the bows, the front end being pivotable laterally to switch the mechanism between the first and second positions.

The switch member may be conveniently actuated by a surgeon's index or second finger without losing control of the jaws of the forceps.

The ratchet mechanism may conveniently include a rack carried by a first bow member and a pawl carried by the second bow member, the rack and pawl being engaged in the locked position of the mechanism and disengaged in the unlocked position.

A spring is preferably arranged to urge the pawl into engagement with the ratchet. Alternatively a spring may urge the ratchet into engagement with the pawl.

In preferred embodiments the switch member includes a formation adapted to form a cam surface extending rearwardly of the pivot to engage a surface of the pawl adapted to form a cam follower; arranged so that the movement of the switch member from the locked to unlocked position urges the pawl away from the ratchet against the action of the spring to disengage the pawl and ratchet. The cam surface may be conveniently provided by a pin or stud depending from the body of the switch.

In an alternative arrangement the cam surface of the switch member may engage the ratchet to urge the latter out of engagement with the pawl. It is desirable that a surgeon can quickly or temporarily release the locking mechanism without need to actuate the switch. Accordingly in an especially preferred embodiment of the invention the switch member may be secured by the pivot to a slideable release member, the release member being mounted to allow axial movement between first and rear positions with respect to the core; wherein in the first position the ratchet member may be moved between the locked and unlocked positions and in the rear position the pawl is released from the ratchet.

The release member may have an upward projection defining a forwardly facing finger grip or other manual engagement surface. Thus a surgeon may easily retract the release member to temporarily disengage the ratchet and pawl. Removal of the surgeon's finger re-engages the locking mechanism.

It is important to note that a single spring acting on the pawl not only engages the pawl with the ratchet but also provides the restoring force urging the sliding member into the forward rest position. This economy of construction facilitates assembly and reduces the number of stressed components employed.

The release member and switch are conveniently disposed longitudinally on the upper centre portion of the handle, to allow easy access. The forward facing engagement surface and upper surface of the switch preferably define a continuous, smooth profile. The forward end of the switch may abut with the release member and cooperate with it to provide a click-stop mechanism or over centre arrangement to prevent accidental dislodgement of the switch during use.

The convenient manipulation of the scissor-like handle and controls afforded by the forceps of this invention gives a surgeon greater freedom to manipulate rotation of the jaws. Rotation through 180° as a single movement is facilitated. As the jaws are bilaterally symmetrical complete freedom of angular orientation of the jaws is thereby attained.

This object is achieved by provision of a rotatable sleeve forward of the switch release member, the sleeve being connected to the actuation rod so that rotation of the sleeve causes rotation of the jaws. The sleeve is preferably provided with radial projections dimensioned to define finger engaging recesses between adjacent projections. In this way the rotation of the jaws is responsive without any slackness to the movement of a surgeon's finger.

A connection for engagement of the forceps to a diathermy power supply may be provided. In preferred embodiments of this invention the diathermy connection member is disposed on the lower side of the mounting core. In this way the power cable may pass unobtrusively beneath the surgeon's wrist and under the arm, rather than over the hand as in previously known arrangements. The diathermy connection extends in a plane generally parallel and below the finger engaging bow portions of the handle.

BRIEF DESCRIPTION OF THE DRAWINGS

The invention is further described by means of example but not in any limitative sense with reference to the accompanying drawings of which.

DETAILED DESCRIPTION

Figure 1:
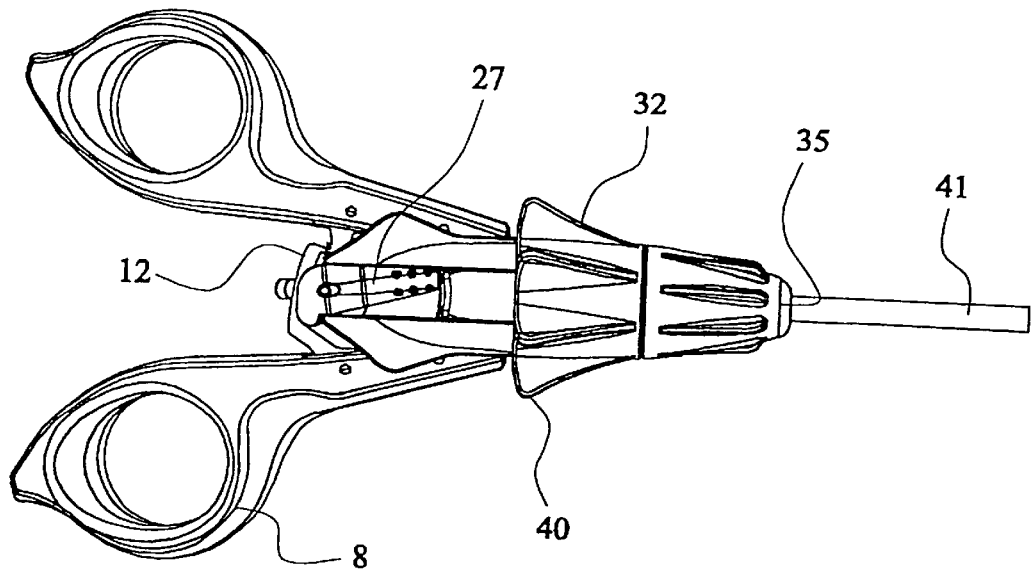
FIG. 1 is a plan view of a laparoscopic forceps handle in accordance with the present invention.

A laparoscopic forceps handle in accordance with this invention is illustrated in FIGS. 1 to 7. The handle described in greater detail below, is connected to the tubular support 41 which carries a conventional jaws assembly (not shown) wherein a pair of jaws mounted on a yoke are actuated by an actuation rod 42 extending within the tubular support 41 from a coupling with a core index sleeve. The tubular support and jaws assembly may be obtained from various commercial sources. The tubular support is releasably fastened to the handle by a universal nut 35.

The handle comprises a core 1 defining a longitudinal channel within which the electro-cautery connection passes. This allows transmission of RF energy from a power supply to the jaws in conventional manner. The core index sleeve includes a rotatable bearing 2 and releasable coupling to the actuation rod 42.

Moulded plastics right and left scissor bows 8, 15 are secured to metal bow inserts 9, 16 pivotally connected to the core 1 by pins 7, 6. Linkages 10, 17 connected to the bows by pins 13, 20 are connected to the connection piece 21 by means of a pin 24 so that opening of the bows causes the actuation rod to be retracted and the jaws to open.

Figure 2:
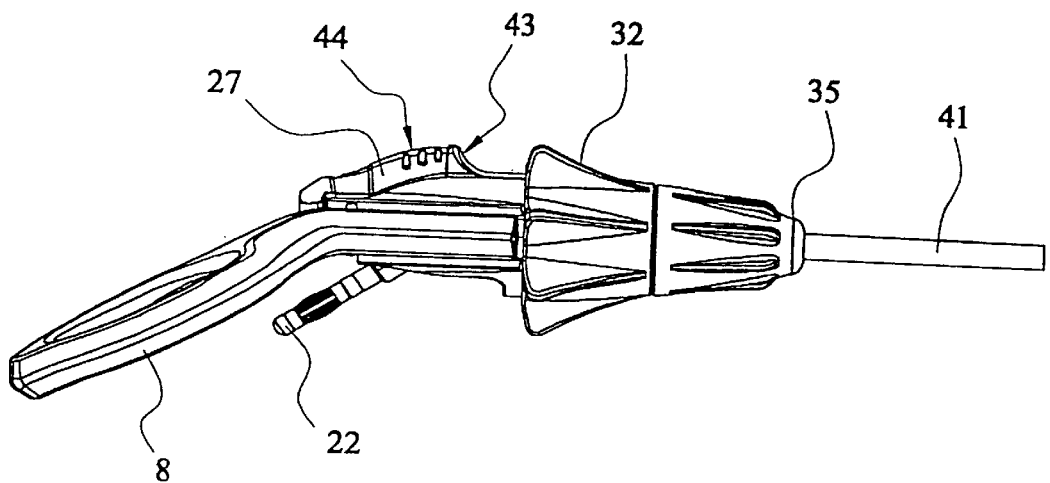
FIG. 2 is a side elevation of the forceps shown in FIG. 1.
Figure 3:
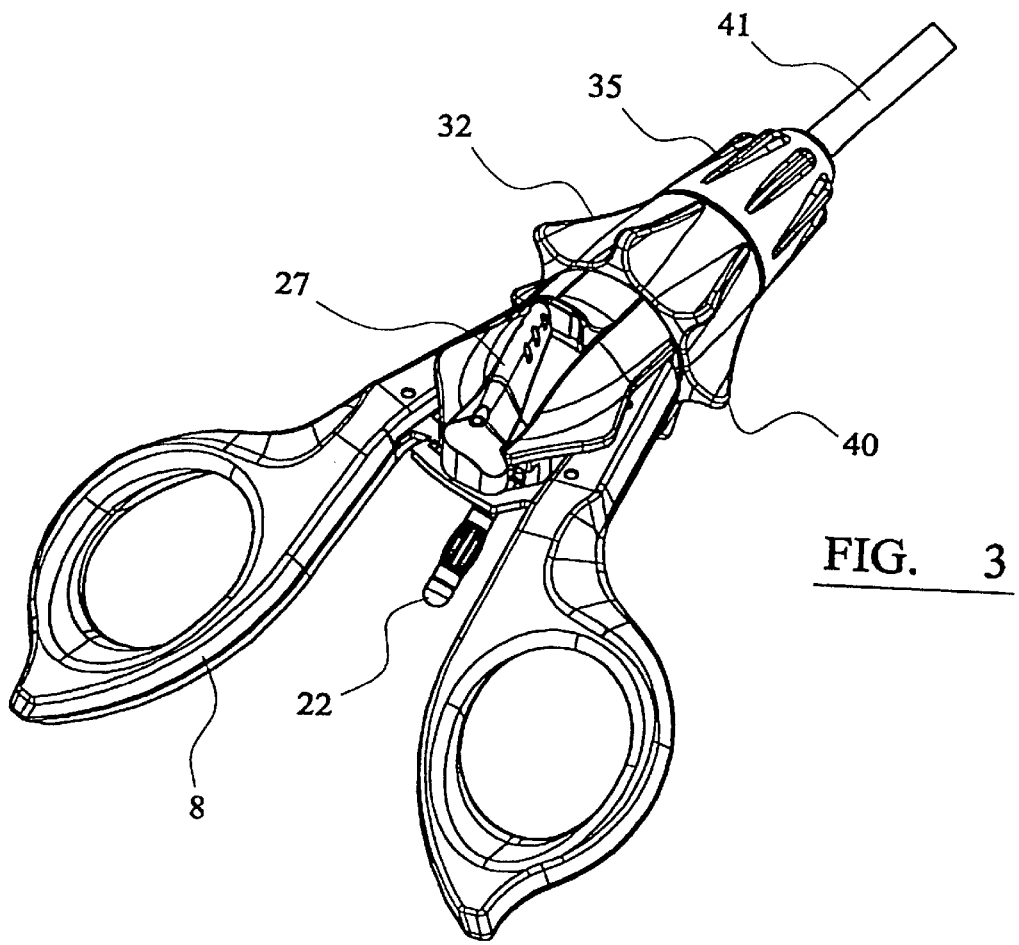
FIG. 3 is an isometric view of the forceps shown in FIG. 1.
Figure 4:
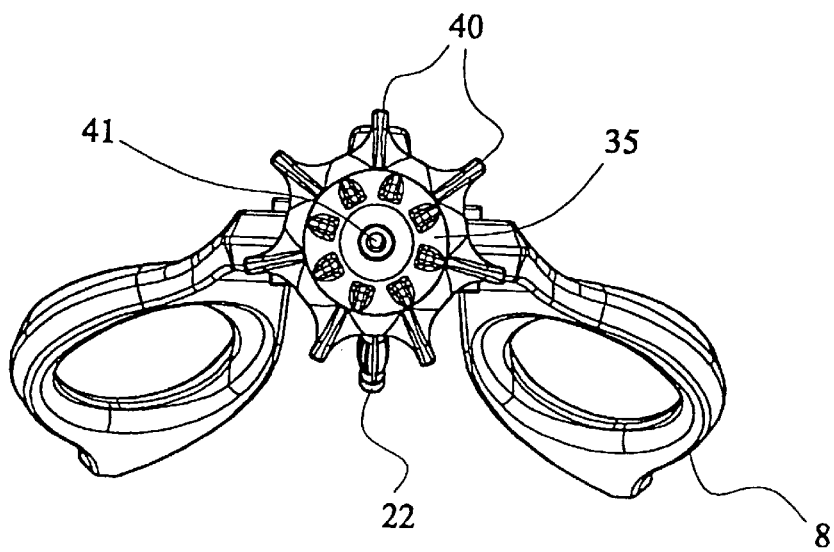
FIG. 4 is a front elevation of the forceps shown in FIG. 1.
Figure 5A:
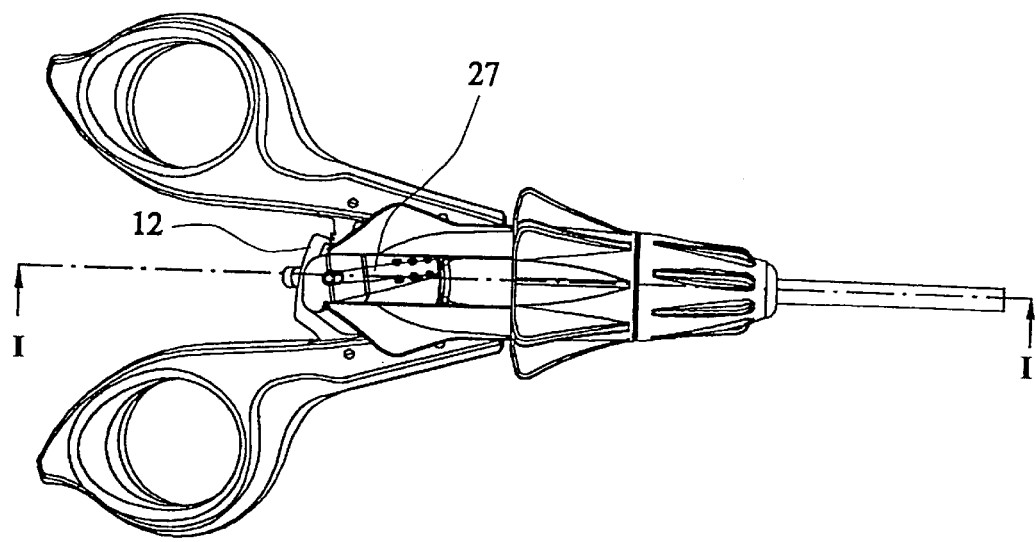
FIG. 5 is a cross-sectional view on I—I.
Figure 5B:
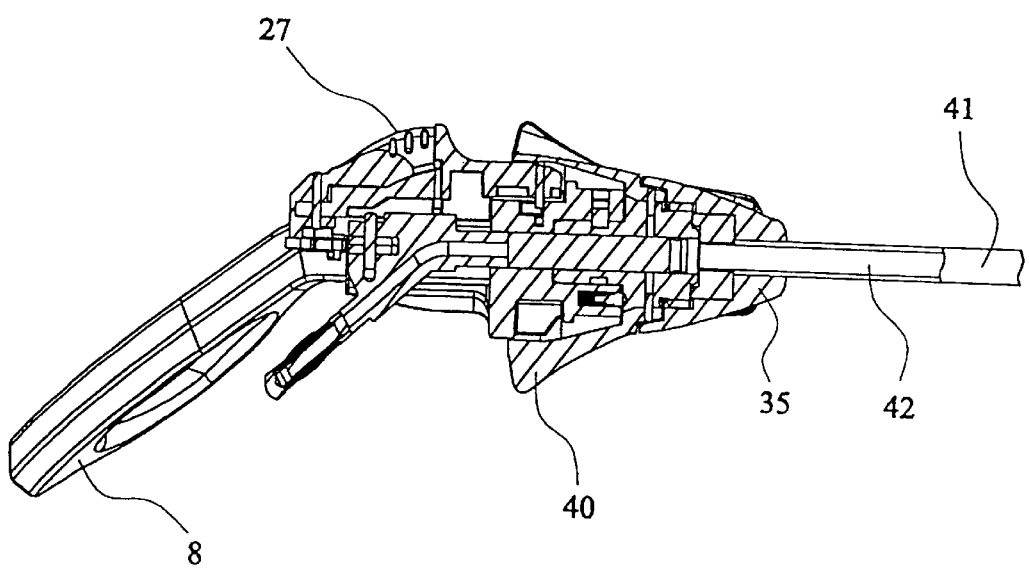

The bows 8, 15 extend downwardly from the horizontal axis of the handle as shown in FIGS. 2 and 4. The angle is selected so that the forceps extend generally coaxially of a user's forearm. This is convenient because the forceps can be rotated simply by rotation of the surgeon's wrist.

The cautery insert rod 22 extends downwards from the centre of the handle generally parallel to the bows 8, 15. The power supply cable connected to rod 22 passes conveniently below a surgeon's wrist in use.

A conical sleeve 32 disposed forwardly of the core 1 and switch assembly is coupled by a pin 34 to the bearing 2. Radial projections 40 are dimensioned so that the index finger may fit snugly between adjacent projections to facilitate rotation of the forceps jaws through an angle up to 180° in a single movement.

The profile 43, 44 of the switch members 25, 27 forms a smooth contour. The forward edge of switch 27 is disposed behind a complementary surface 46 of a slideable release member 25. A plunger 28 and spring 29 engage recesses in surface 46 to provide positive engagement of the switch in the left and right positions.

Ratchet 19 and pawl 12 are carried by bow inserts 16 and 9 respectively. Ratchet 19 is fixed but pawl 12 is pivotally connected by a pin 13 and bias forwardly by the pawl return spring 14. The teeth of the ratchet 19 are arranged so that when pawl 12 engages the ratchet the jaws may be closed but not opened.

The ratchet may be released by rearward movement of the slideable release member 25 which carries a switch 27 secured to the rear end thereof by pin 31. The member 25 is slidably mounted on a longitudinal formation on the upper surface of connection piece 21. Rearward movement of member 25 by pressure on the forward facing surface 43 moves the switch 27 rearwardly.

Switch 27 has a downwardly depending pin or stud 30 which acts as a pawl release guide. The pin 30 is laterally offset so that left to right movement of the switch moves the pin rearwardly and movement from right to left moves the pin forwardly. The pin 30 engages the forward surface of pawl member 12 to form a cam and cam follower arrangement.

The operation of the forceps handle is described with reference to FIGS. 6 and 7. FIGS. 6a to 6d show partial views of the switch assembly B.

Figure 6A:
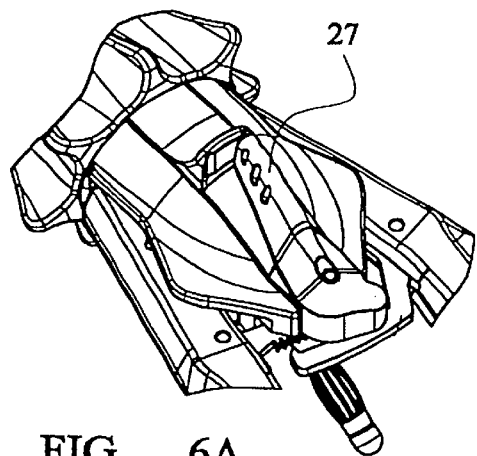
FIG. 6 is a series of partial views illustrating operation of the handle.
Figure 6B:
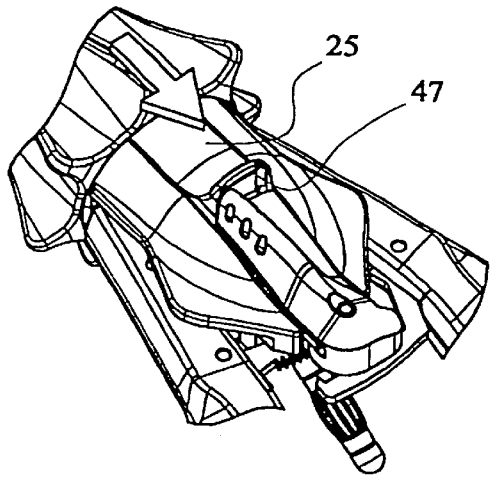
Figure 7:
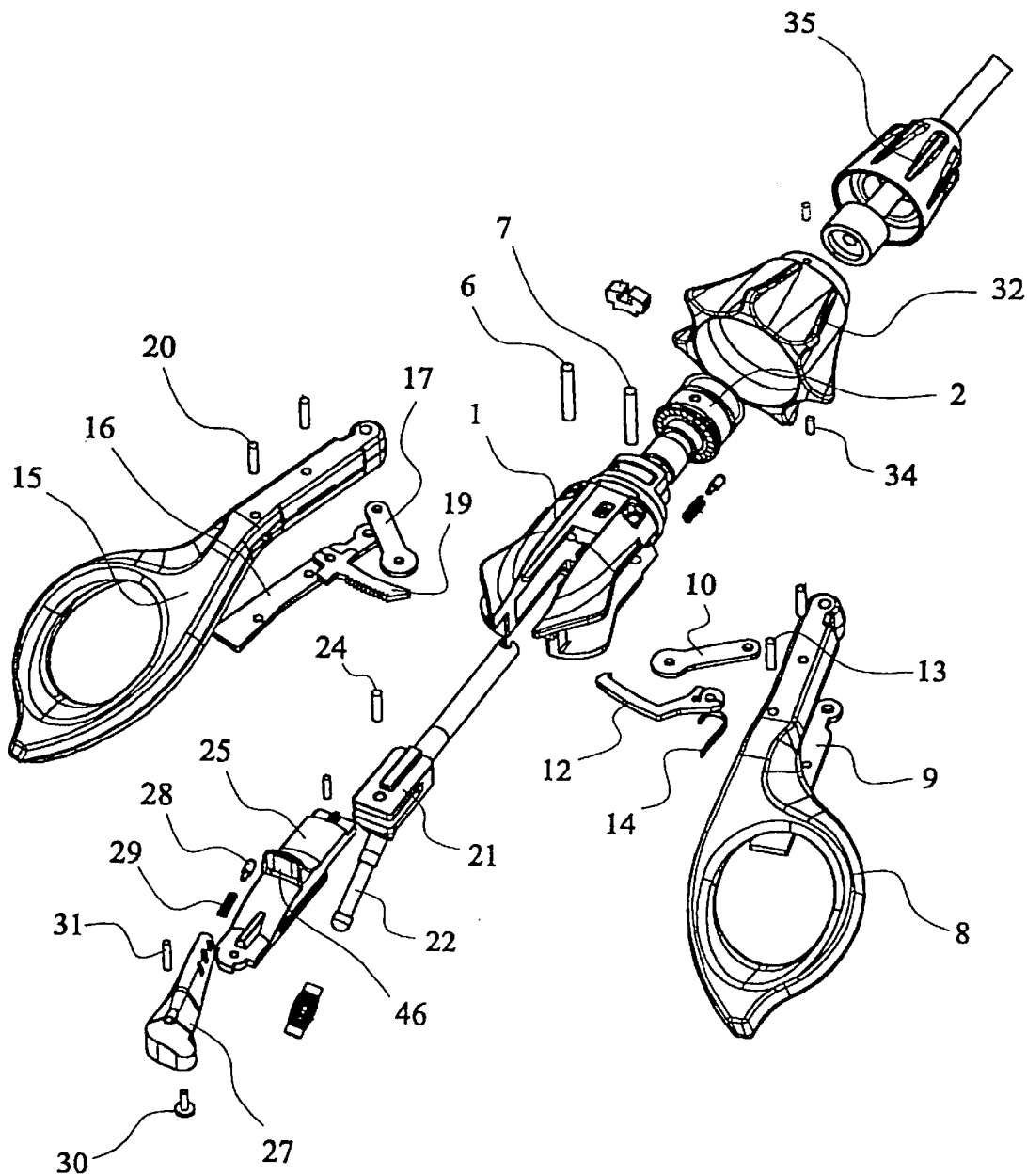
FIG. 7 is an exploded view of forceps in accordance with this invention.

In FIG. 6a the switch 27 is in the right-hand position. The plunger 28 is engaged in the right hand recess 47 in surface 46.

The pin 30 is at the most rearwardly position and bears against the forward surface of pawl member 12 disengaging the latter from the ratchet 19.

Figure 6C:
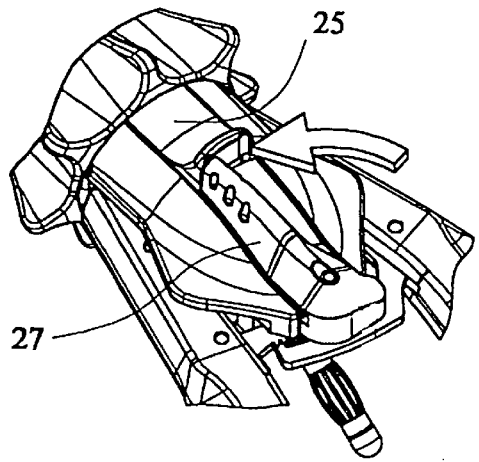
Figure 6D:
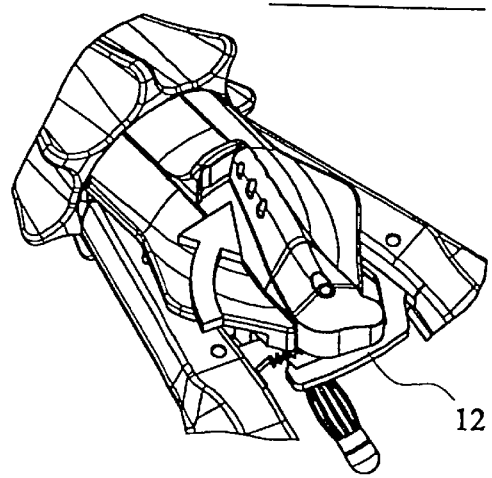
Figure 6:
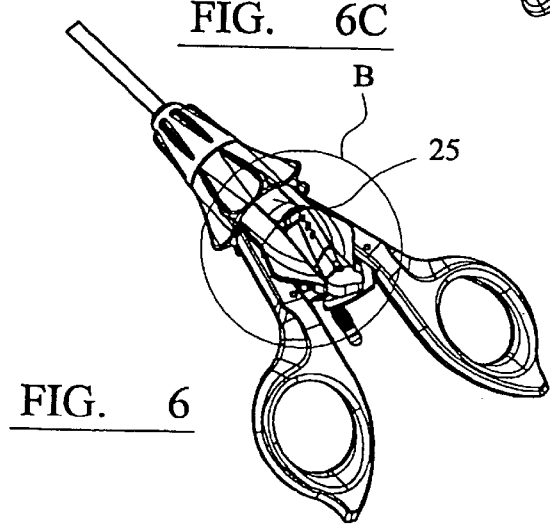

Movement of the switch 27 to the left, as shown in FIG. 6c moves pin 30 forwardly allowing spring 14 to urge the pawl into engagement with the ratchet preventing opening of the forceps jaws. Movement of the switch 27 to the right as shown in FIG. 6d releases the pawl permitting opening of the jaws.

FIG. 6b illustrates a quick temporary release of the pawl by sliding member 25 in a rearward direction. Pin 30 pushes pawl 12 directly rearwardly allowing free use of the jaws. Release of the member 25 re-engages the ratchet mechanism.

What is claimed is:

1. A laparoscopic forceps comprising;
    a handle comprising left and right bow members pivotally connected to a mounting core and adapted to engage a finger and thumb;
    a tubular housing extending axially from the handle and carrying an actuation rod;
    a jaws mechanism disposed at the end of the tubular housing remote from the handle engaged to the actuation rod and arranged so that the jaws may be opened or closed by actuation of the handle;
    a switch mechanism moveable between locked and unlocked positions, adapted when locked to allow closure and prevent opening of the jaws, and when unlocked to allow free opening and closing of the jaws; and
    a slideable release member having a first position and a release position, wherein said slidable release member, while in said release position, permits free opening of the jaws with the bow members while said switch mechanism is in the locked position.

2. A laparoscopic forceps as claimed in claim 1, wherein the switch mechanism incorporates a finger operable switch member.

3. A laparoscopic forceps as claimed in claim 2, wherein the switch member is located on the upper side of the mounting core of the handle.

4. A laparoscopic forceps as claimed in claim 3, wherein the switch extends longitudinally along the handle and is engaged by a pivot at the rear end thereof between the bows, the front end being pivotable laterally to switch the mechanism between the first and second positions.

5. A laparoscopic forceps as claimed in claim 1, wherein the switch mechanism incorporates a finger operable switch member, and further includes a ratchet carried by a first bow member and a pawl carried by the second bow member, the ratchet and pawl being engaged in the locked position of the mechanism and disengaged in the unlocked position.

6. A laparoscopic forceps as claimed in claim 5, wherein a spring is arranged to urge the pawl into engagement with the ratchet.

7. A laparoscopic forceps as claimed in claim 6, wherein the switch member includes a formation adapted to form a cam extending rearwardly of the pivot to engage a surface of the pawl adapted to form a cam follower, arranged so that the movement of the switch member from the locked to unlocked position urges the pawl away from the ratchet against the action of the spring to disengage the pawl and ratchet.

8. A laparoscopic forceps as claimed in claim 7, wherein the cam comprises a pin or stud depending from the body of the switch.

9. A laparoscopic forceps as claimed in claim 7, wherein the switch member may engage the ratchet in use to urge the latter out of engagement with the pawl.

10. A laparoscopic forceps as claimed in claim 5, wherein the switch member is secured by a pivot to the slidable release member, the release member being mounted to allow axial movement between forward and rear positions with respect to the core; wherein in the forward position the ratchet member may be moved between the locked and unlocked positions and in the rear position the pawl is released from the ratchet.

11. A laparoscopic forceps as claimed in claim 10, wherein the release member may have an upward projection defining a forwardly facing finger grip or other manual engagement surface.

12. A laparoscopic forceps as claimed in claim 10, wherein the release member and switch are disposed longitudinally on the upper centre portion of the handle.

13. A laparoscopic forceps as claimed in claim 12, wherein a forward facing engagement surface and upper surface of the switch define a continuous, smooth profile.

14. A laparoscopic forceps as claimed in claim 10, including a rotatable sleeve forward of the switch release member, the sleeve being connected to the actuation rod so that rotation of the sleeve causes rotation of the jaws.

15. A laparoscopic forceps as claimed in claim 1, wherein said first angle is selected such that said forceps comprise a coaxial extension of the forearm of a forceps user.

16. A laparoscopic forceps as claimed in claim 1, wherein said left and right bow members are adapted such that each is located on an opposite side of said longitudinal axis of said handle.

17. A laparoscopic forceps comprising:

a handle comprising left and right bow members pivotally connected to a mounting core and adapted to engage a finger and thumb;

a tubular housing extending axially from the handle and carrying an actuator rod;

a jaws mechanism disposed at the end of the tubular housing remote from the handle engaged to the actuator rod and arranged so that the jaws may be opened or closed by actuation of the handle; and a switchable ratchet mechanism moveable between locked and unlocked positions, adapted when locked to allow closure and prevent opening of the jaws, and when unlocked to allow free opening and closing of the jaws, wherein the switchable ratchet mechanism incorporates a finger operable switch member, said finger operable switch member being independently operable in both lateral and axial directions relative to said mounting core.

18. A laparoscopic forceps as claimed in claim 17, wherein the switch extends longitudinally along the handle and is engaged by a pivot at the rear end thereof between the bows, the front end being pivotable laterally to switch the mechanism between the first and second positions.

19. A laparoscopic forceps comprising a handle; a tubular housing extending axially from the handle and carrying an actuation rod; a jaws mechanism disposed at the end of the tubular housing remote from the handle engaged to the actuation rod and arranged so that the jaws may be opened or closed by actuation of the handle; wherein the handle comprises left and right bow members pivotally connected to a mounting core and adapted to engage a user's finger and thumb in use;

the forceps including a switchable ratchet mechanism moveable between locked and unlocked positions, adapted when locked to allow closure and prevent opening of the jaws, and when unlocked to allow free opening and closing of the jaws, wherein the switchable ratchet mechanism incorporates a finger operable switch member, and further includes a ratchet carried by a first bow member and a pawl carried by the second bow member, the ratchet and pawl being engaged in the locked position of the mechanism and disengaged in the unlocked position, wherein the switch member is secured by a pivot to a slidable release member, the release member being mounted to allow axial movement between forward and rear positions with respect to the core; wherein in the forward position the ratchet member may be moved between the locked and unlocked positions and in the rear position the pawl is released from the ratchet.

20. A laparoscopic forceps as claimed in claim 19, wherein the release member and switch are disposed longitudinally on the upper centre portion of the handle.

* * * * *